(12) United States Patent
Ichikawa et al.

(10) Patent No.: US 9,044,357 B2
(45) Date of Patent: Jun. 2, 2015

(54) DISPOSABLE WEARING ARTICLE

(75) Inventors: Makoto Ichikawa, Kanonji (JP);
Kenichi Sasayama, Kanonji (JP);
Kunihiko Katsuragawa, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 189 days.

(21) Appl. No.: 13/810,858

(22) PCT Filed: Aug. 31, 2011

(86) PCT No.: PCT/JP2011/004850
§ 371 (c)(1),
(2), (4) Date: Jan. 17, 2013

(87) PCT Pub. No.: WO2012/029294
PCT Pub. Date: Mar. 8, 2012

(65) Prior Publication Data
US 2013/0123736 A1    May 16, 2013

(30) Foreign Application Priority Data
Aug. 31, 2010   (JP) .................................. 2010-195012

(51) Int. Cl.
*A61F 13/15*    (2006.01)
*A61F 13/49*    (2006.01)
(Continued)

(52) U.S. Cl.
CPC . *A61F 13/49014* (2013.01); *A61F 2013/49026* (2013.01); *A61F 13/49011* (2013.01);
(Continued)

(58) Field of Classification Search
CPC ..................... A61F 13/49011; A61F 13/49058; A61F 13/4906; A61F 13/49061; A61F 13/49466; A61F 13/49473; A61F 2013/49025; A61F 2013/49026; A61F 2013/49033; A61F 2013/49098; A61F 2013/49493

USPC ................ 604/385.19, 385.29, 385.3, 385.31
See application file for complete search history.

(56) References Cited

U.S. PATENT DOCUMENTS 7,322,967 B2 *   1/2008   Kondo ..................... 604/385.29
7,785,309 B2 *   8/2010   Van Gompel et al. . 604/385.101
(Continued)

FOREIGN PATENT DOCUMENTS

EP    1366734 A1    12/2003
JP    7-184947 A    7/1995
(Continued)

OTHER PUBLICATIONS

Supplementary European Search Report issued May 13, 2014, corresponds to European patent application No. 11821315.6.
(Continued)

*Primary Examiner* — Lynne Anderson
(74) *Attorney, Agent, or Firm* — Lowe Hauptman & Ham, LLP

(57) ABSTRACT

A diaper includes front and rear waist members and a crotch member. The front and rear waist members are respectively formed with first narrowly-spaced elastic zones, widely-spaced elastic zones and second narrowly-spaced elastic zones adjacent one to another. Front and rear ends of the crotch member are bonded to respective sides of the front and rear waist members so that the crotch member's front and rear ends may positionally correspond to the second narrowly-spaced elastic zones. Cover sheets are attached to the side of the crotch member to cover the crotch member's front and rear ends respectively. A length dimension of the cover sheet in the longitudinal direction is set to be smaller than those of the front and rear waist members and a length dimension of the cover sheet in the transverse direction is substantially equal to those of the front and rear waist members.

18 Claims, 6 Drawing Sheets

(51) Int. Cl.
  *A61F 13/496* (2006.01)
  *A61F 13/514* (2006.01)
  *A41B 9/00* (2006.01)
  *A61F 13/64* (2006.01)

(52) U.S. Cl.
  CPC ......... *A61F13/49017* (2013.01); *A61F 13/496* (2013.01); *A61F 13/51478* (2013.01); *A41B 9/00* (2013.01); *A61F 13/49058* (2013.01); *A61F 13/49061* (2013.01); *A61F 13/64* (2013.01)

(56) References Cited

U.S. PATENT DOCUMENTS

| | | | |
|---|---|---|---|
| 2002/0138065 A1* | 9/2002 | Yeater et al. | 604/395 |
| 2005/0177125 A1 | 8/2005 | Kondo | |
| 2011/0060306 A1* | 3/2011 | Otsubo | 604/385.21 |
| 2011/0077609 A1* | 3/2011 | Kuwano et al. | 604/385.01 |
| 2012/0035572 A1* | 2/2012 | Ichikawa et al. | 604/385.3 |
| 2012/0226254 A1* | 9/2012 | Takino | 604/385.3 |
| 2012/0271266 A1* | 10/2012 | Sasayama et al. | 604/385.24 |
| 2013/0012905 A1* | 1/2013 | Katsuragawa et al. | 604/385.3 |
| 2013/0123735 A1* | 5/2013 | Ichikawa et al. | 604/385.19 |
| 2013/0123737 A1* | 5/2013 | Nakajima | 604/385.24 |

FOREIGN PATENT DOCUMENTS

| | | |
|---|---|---|
| JP | 4240463 B2 | 11/2004 |
| JP | 2005270377 A | 10/2005 |
| JP | 2006-247009 A | 9/2006 |
| JP | 2009-207778 A | 9/2009 |
| WO | 2007144838 A1 | 12/2007 |

OTHER PUBLICATIONS

International Search Report and Written Opinion corresponding to PCT/JP2011/004850, dated Nov. 15, 2011.

* cited by examiner

DISPOSABLE WEARING ARTICLE

RELATED APPLICATIONS

The present application is a National Phase of International Application Number PCT/JP2011/004850, filed Aug. 31, 2011, and claims priority from Japanese Application Number 2010-195012, filed Aug. 31, 2010.

TECHNICAL FIELD

The present disclosure relates to disposable wearing articles and, more particularly, to various types of disposable wearing articles, such as disposable diapers, disposable toilet-training pants, disposable incontinent pants and disposable sanitary napkins.

BACKGROUND ART

Disposable diapers including belt-like members defining front and rear waist regions, respectively, and an absorbent structure bonded to these belt-like members are known. For example, JP 4240463 B2 (PTL 1) discloses a diaper in which the front and rear ends of absorbent structure are bonded to the sides of the respective belt-like members facing away from the wearer's body. According to this disclosure, an outer sheet is bonded to the sides of the respective belt-like members facing away from the wearer's body by the intermediary of the absorbent structure. The outer sheet bonded to the belt-like members in this manner functions to prevent the front and rear ends of the absorbent structure from being curled up and thereby to improve the appearance of the diaper. In addition, the outer sheet bonded to the belt-like members functions also to prevent the front and rear ends of the absorbent structure from being caught by the wearer's garment and eventually functions to prevent the absorbent structure from being peeled off from the belt-like members of the diaper.

CITATION LIST

Patent Literature

{PTL 1} JP 4240463 B2

SUMMARY OF INVENTION

Technical Problem

In the diaper described above, the outer sheet is the same as each of the belt-like members in shape as well as in size. The inventor (s) have recognized that, as a consequence, air-permeability of the belt-like members may correspondingly degrade and cause the wearer to suffer from diaper rash due to stuffiness within the diaper particularly because these belt-like members are elastically stretchable and contractible and apt to come in close contact with the wearer's waist.

Solution to Problem

According to one or more aspects of the present invention, there is provided a disposable wearing article having longitudinal and transverse directions and including a body-facing side for facing the wearer's body, a garment-facing side for facing away from the wearer's body, front and rear waist regions and a crotch region extending between the front and rear waist regions in the longitudinal direction, front and rear waist members defining the front and rear waist regions, respectively, and a crotch member defining the crotch region and joined to the front and rear waist members.

The crotch member has front and rear ends extending in the transverse direction. At least the front and rear ends are joined to the garment-facing side of the front and rear waist members, respectively. The crotch member is provided on the garment-facing side with cover sheets that cover the front and rear ends of the crotch member. A length dimension of the cover sheets in the longitudinal direction is smaller than those of the front and rear waist members.

Advantageous Effects of Invention

According to one or more embodiments, the crotch member is bonded to the respective sides of the front and rear waist members facing away from the wearer's body and the length dimension in the longitudinal direction of the cover sheets adapted to cover the front and rear ends of the crotch member is set to be smaller than those of the front and rear waist members. With such arrangements, it is possible to form regions not covered with the cover sheets in the front and rear waist members and thereby to assure high air-permeability of the front and rear waist members at least in these regions.

BRIEF DESCRIPTION OF DRAWINGS

One or more aspects will be more fully understood and further advantages become apparent when reference is made to the following detailed description of one or more embodiments and the accompanying drawing, in which:

In FIGS. 3 through 6, respective elastics are shown in a stretched state against contractile forces thereof. The diaper has an imaginary longitudinal center line P-P bisecting a width dimension of the diaper in a transverse direction X and an imaginary transverse center line Q-Q bisecting a length dimension of the diaper in a longitudinal direction Y wherein the diaper is substantially symmetric about the imaginary longitudinal center line P-P. In the accompanying drawings, respective ones of paired reference signs in the symmetric parts are partially omitted.

DESCRIPTION OF EMBODIMENTS

Figure 1:
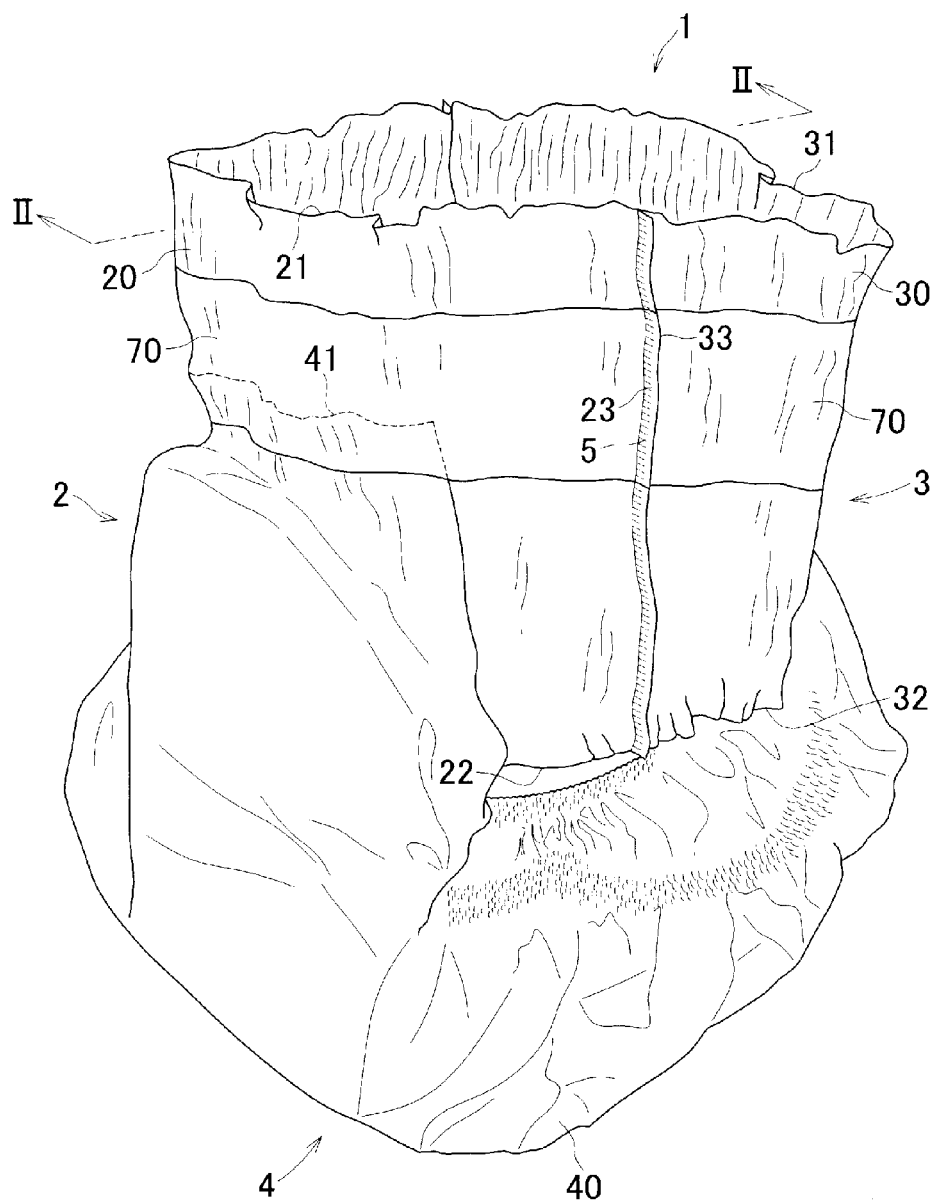
FIG. 1 A perspective view of a diaper as an example of a disposable wearing article according to an embodiment of the present invention.

Referring to FIG. 1, a diaper 1 has a body-facing side for facing the wearer's body, a side opposite thereto (i.e., a garment-facing side for facing the wearer's garment), a front waist region 2, a rear waist region 3 and a crotch region 4 extending between the front and rear waist regions 2, 3 wherein these regions are continuous in a longitudinal direction Y. The diaper 1 includes front and rear waist members 20, 30 defining the front and rear waist regions 2, 3, respectively, and a crotch member 40 defining the crotch region 4. The front and rear waist members 20, 30 are respectively contoured by front and rear outer ends 21, 31 spaced from each other in a longitudinal direction Y and extending in a transverse direction X (see FIG. 3), front and rear inner ends 22, 32 positioned between the front and rear outer ends 21, 31 and extending in the transverse direction X, and front and rear waist side edges 23, 33 extending in the longitudinal direction Y. The front and rear waist members 20, 30 are joined to each other at seams 5 arranged intermittently along the respective side edges 23, 33 thereof and thereby the front and rear waist members 20, 30 are maintained in an annular shape.

Figure 2:
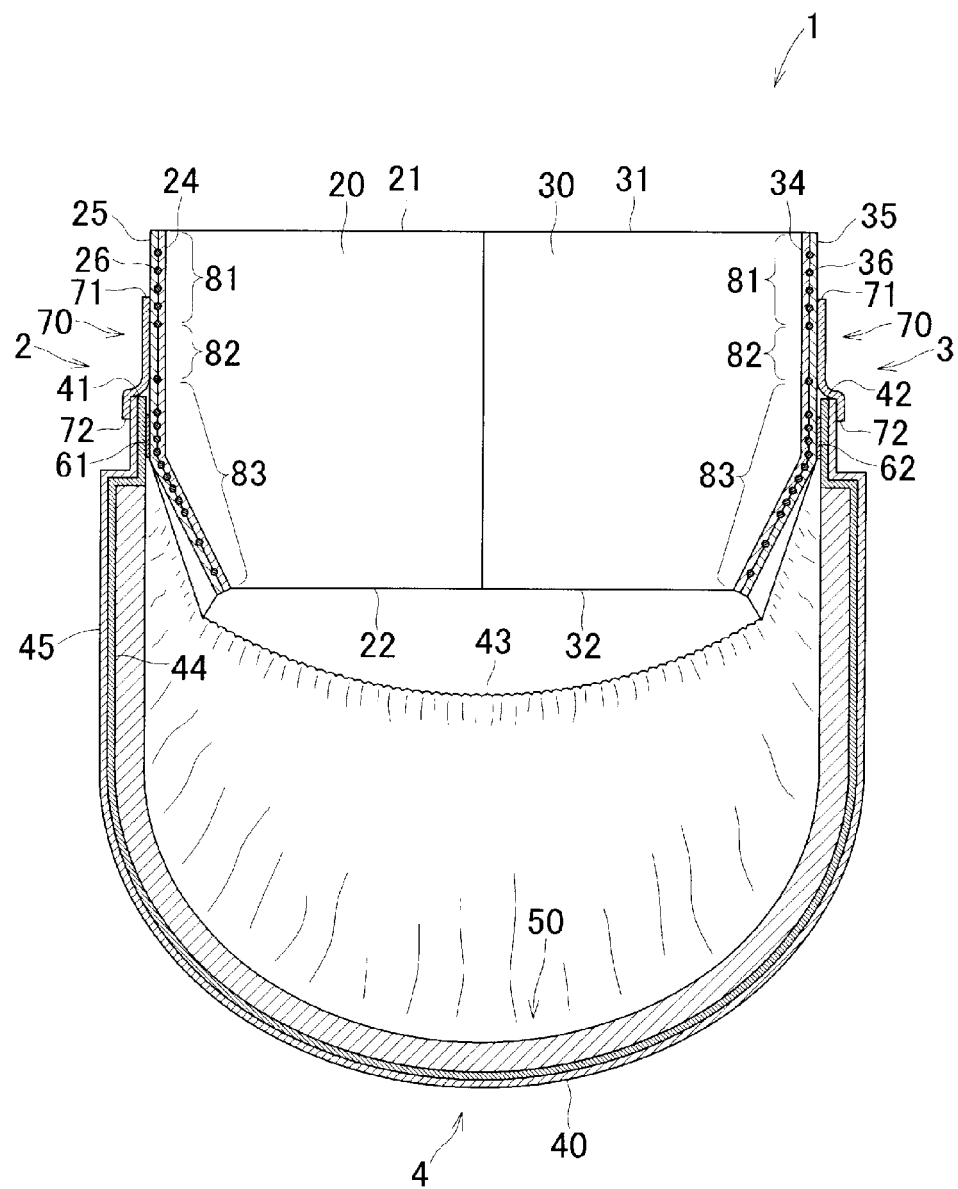
FIG. 2 A sectional view taken along line II-II in FIG. 1.
Figure 3:
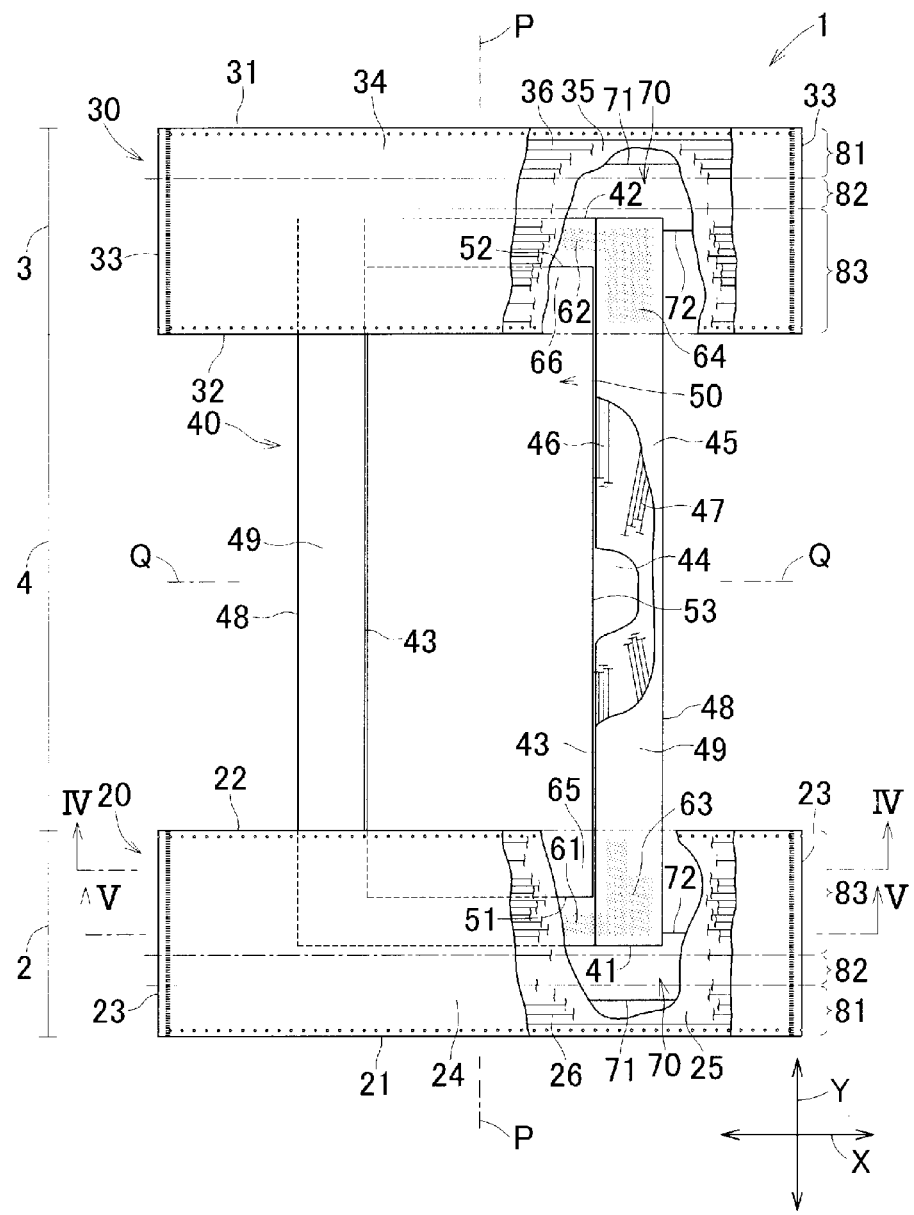
FIG. 3 A developed plan view of the diaper.

Referring now to FIGS. 2 and 3, the front and rear waist members 20, 30 respectively include inner sheets 24, 34 for facing the wearer's body, outer sheets 25, 35 opposite to the respective inner sheets 24, 34, i.e., for facing away from the wearer's body, and a plurality of front and rear waist elastics 26, 36 sandwiched between these inner and outer sheets, respectively. The front and rear waist inner sheets 24, 34 and the front and rear waist outer sheets 25, 35 may be formed, for example, of fibrous nonwoven fabrics each having a mass per unit area (i.e., a basis mass) about 10 to about 30 g/m$^2$. The front and rear waist elastics 26, 36 respectively spaced one from another in the longitudinal direction Y and may be contractibly attached under tension and in the transverse direction X to the front and rear waist members 20, 30 so as to elasticize the front and rear waist members 20, 30 in the transverse direction X. The front and rear waist elastics 26, 36 may be implemented in the form of yarns or threads. These front and rear waist elastics 26, 36 be bonded to at least one of the inner and outer sheets constituting each of the front and rear waist members with hot melt adhesives (not shown).

The front and rear waist members 20, 30 respectively have narrowly-spaced elastic zones in which the front and rear waist elastics 26, 36 are arranged at a relatively small pitch in the longitudinal direction Y and widely-spaced elastic zones in which those elastics 26, 36 are arranged at a relatively large pitch in the longitudinal direction Y. First narrowly-spaced elastic zones 81, widely-spaced elastic zones 82, and second narrowly-spaced elastic zones 83 are adjacent one to another from the outer ends 21, 31 of the front and rear waist members 20, 30 to the inner ends 22, 32 of the front and rear waist member 20, 30, respectively, in this order. It should be noted here that, in respective sections of the second narrowly-spaced elastic zones 83 being adjacent to the crotch region 4, the front and rear waist member elastics 26, 36 are arranged at a relatively small pitch. Specifically, five elastic yarns or threads each having fineness of about 940 dtex are arranged at a pitch of about 8 mm in each of the first narrowly-spaced elastic zones 81, and twelve elastic yarns or threads each having fineness of about 780 to about 940 dtex are arranged at a pitch of about 6 mm to about 15 mm in each of the second narrowly-spaced elastic zones 83. In the widely-spaced elastic zones 82, the front and rear waist elastics 26, 36 are arranged at a pitch of about 25 mm. In this manner, the first and second narrowly-spaced elastic zones 81, 83 and the widely-spaced elastic zones 82 are respectively defined by the front and rear waist elastics 26, 36. The term "pitch" of "spacing" used herein means a dimension between the center of one elastic as measured in the longitudinal direction Y to the center of the adjacent elastic as measured in the longitudinal direction Y.

The crotch member 40 is contoured by front and rear ends 41, 42 extending in the transverse direction X and transversely opposite side edge portions 43 extending in the longitudinal direction Y, and includes an inner sheet 44 for facing the wearer's body, an outer sheet 45 for facing the wearer's garment, and first and second crotch elastics 46, 47 respectively sandwiched between the inner and outer sheets 44, 45. The inner sheet 44 may be formed of a liquid-impervious but moisture-pervious plastic film and the outer sheet 45 may be formed of a liquid-impervious fibrous nonwoven fabric.

The side edge portions 43 of the crotch member 40 are folded inward in the transverse direction X along respective fold lines 48 extending in the longitudinal direction Y to define respective folded regions 49 in which the inner sheet 44 of the crotch member 40 faces itself. In these folded regions 49, the inner sheet 44 of the crotch member 40 are bonded to itself with hot melt adhesives or the like (not shown).

The first and second crotch elastics 46, 47 may be respectively provided in the form of two or more yarns or threads and may be attached under tension and in a contractible manner in the longitudinal direction Y to the crotch member 40 to elasticize the side edge portions 43 in the longitudinal direction Y. The first crotch elastics 46 are attached to the crotch member 40 along its transversely opposite side edges 53 of a liquid-absorbent structure 50 described later. The second crotch elastics 47 are attached to the crotch member 40 adjacent to the fold lines 48. Segments of the second crotch elastics 47 between the side edges 53 of the absorbent structure 50 and the fold lines 48 are curved from the fold lines 48 in the vicinities of the front and rear and rear ends 41, 42 toward an imaginary line Q-Q. The first and second crotch elastics 46, 47 are bonded to at least one of the inner and outer sheets 44, 45 of the crotch member 40 with hot melt adhesives or the like (not shown).

Figure 4:
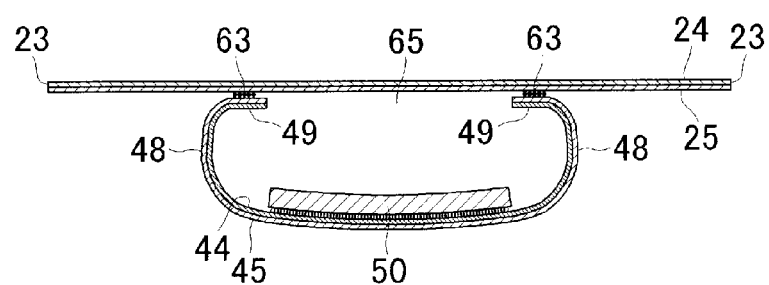
FIG. 4 A sectional view taken along line IV-IV in FIG. 3.
Figure 5:
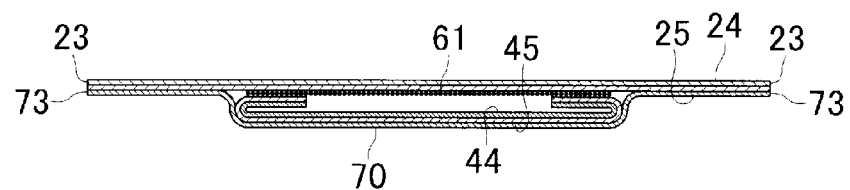
FIG. 5 A sectional view taken along line V-V in FIG. 3.
Figure 6:
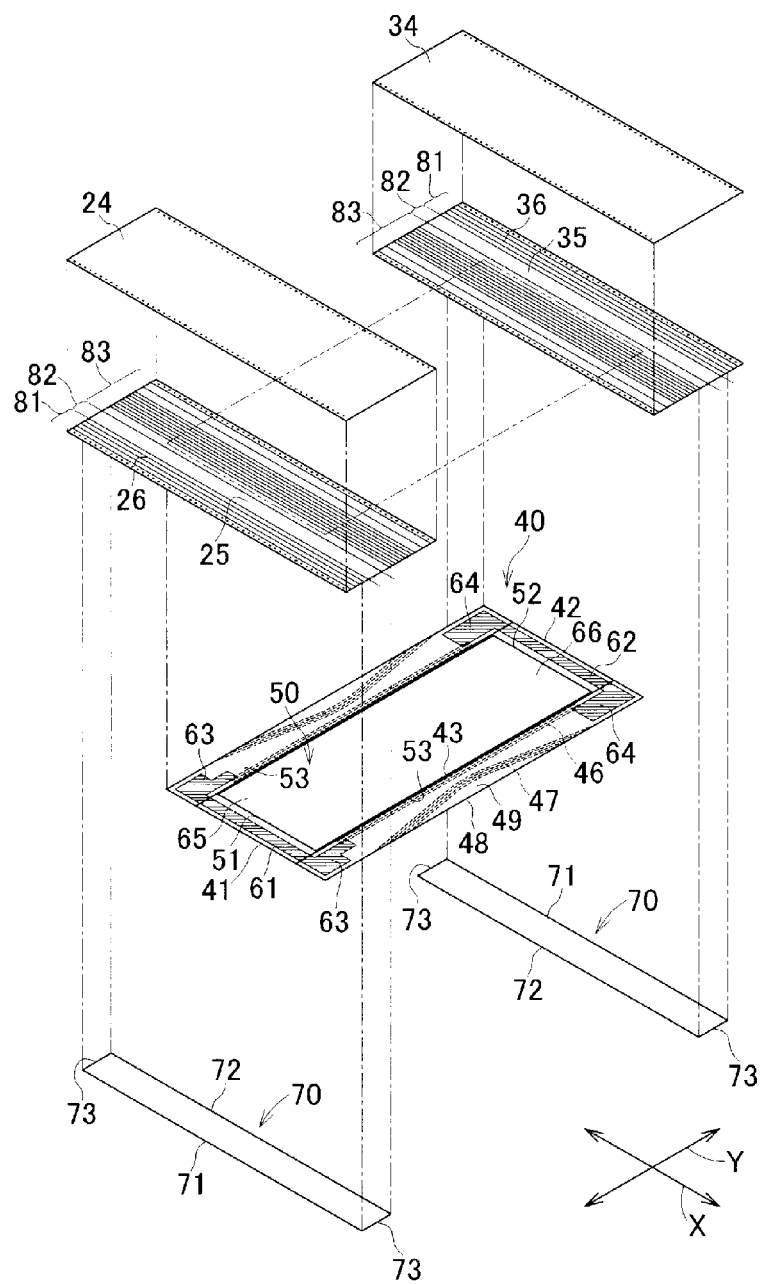
FIG. 6 A exploded perspective view of the diaper.

The liquid-absorbent structure 50 is placed on the body-facing side of the crotch member 40. The liquid-absorbent structure 50 includes liquid-absorbent core materials, such as fluff pulp, super-absorbent polymer particles or a mixture thereof, and a wrapping sheet that wraps core materials. The liquid-absorbent structure 50 is contoured by front and rear ends 51, 52 extending in the transverse direction X and the transversely opposite side edges 53 extending in the longitudinal direction Y. In the liquid-absorbent structure 50, front and rear ends 51, 52 lie between the front and rear ends 41, 42 of the crotch member 40 in the longitudinal direction Y, and the side edges 53 of the liquid-absorbent structure 50 lie between the fold lines 48 in the transverse direction X (See FIGS. 3 and 4).

The liquid-absorbent structure 50 is bonded to the crotch member 40 by bonding means, such as hot melt adhesives (not shown). The liquid-absorbent structure 50, which is relatively bulky, lies between the fold lines 48 as viewed in the transverse direction X and, therefore, as a whole, the crotch region 4 does not become bulky due to the presence of the liquid-absorbent structure 50. The first and second crotch elastics 46, 47 are attached outboard of the liquid-absorbent structure 50 as viewed in the transverse direction X so that the side edge portions 43 of the crotch member 40 are elasticized by these elastics to whereby come in close contact with the wearer's thighs and prevent body waste, such as urine, from leaking out.

In the crotch member 40, at least the front and rear ends 41, 42 are bonded to the respective garment-facing sides of the front and rear waist members 20, 30 with hot melt adhesives or the like. Specifically, between the crotch member 40 and the respective outer sheets 25, 35 of the front and rear waist members 20, 30, first bonded regions 61, 62 extending in the transverse direction X along the front and rear ends 41, 42 of the crotch member 40, and second bonded regions 63, 64 extending in the longitudinal direction Y on both transversely opposite sides of the first bonded regions 61, 62 are formed.

In the first bonded regions 61, 62, the crotch member's inner sheet 44 is bonded along its front and rear ends 41, 42 to the outer sheets 25, 35 of the front and rear waist members 20, 30 and, in the second bonded regions 63, 64, the outer sheet 45 of the crotch member 40 have its folded regions 49 bonded to the outer sheets 25, 35 of the front and rear waist members 20, 30. Respective length dimensions of the second bonded regions 63, 64 in the longitudinal direction Y are larger than those of the first bonded regions 61, 62. The second bonded regions 63 in the front waist region 2 respectively have width dimensions in the transverse direction X which are stepwise reduced in the vicinity of the crotch region 4. It is also possible to form the respective second bonded regions 63 as slops inclining toward the imaginary longitudinal center line P-P and toward the crotch region 4 to gradually reduce the width dimensions of these bonded regions 63. Between the second bonded regions 63, 64 in the transverse direction X, non-bonded regions 65, 66 not being coated with adhesives or the like are defined. These non-bonded regions 65, 66 are defined substantially in a central area as viewed in the transverse direction X and pockets (best seen in FIG. 4) are defined in the respective front and rear waist regions 2, 3 by the first and second bonded regions 61, 62, 63, 64 and the non-bonded regions 65, 66. The pockets have openings directed toward the crotch region 4.

The crotch member 40 are attached to the front and rear waist members 20, 30 so that the front and rear ends 41, 42 of the crotch member 40 may respectively overlap the second narrowly-spaced elastic zones 83. The crotch member 40 is, therefore, positioned from the respective widely-spaced elastic zones 82 toward the crotch region 4. When the diaper 1 is put on the wearer's body, the widely-spaced elastic zones 82 in which the front and rear waist elastics 26, 36 are arranged at a large pitch facilitate the helper or user to grasp the front and rear waist members 20, 30 and to pull up or down the diaper 1. More specifically, the helper or user can easily get his or her fingers caught in the respective widely-spaced elastic zones 82. The front and rear ends 41, 42 of the crotch member 40 are attached to the front and rear waist members 20, 30, respectively, from the widely-spaced elastic zones 82 toward the crotch region 4, and with such unique arrangement, the widely-spaced elastic zones 82 should not become unacceptably stiff due to the presence of the crotch member 40, so that the helper or user can easily get his or her fingers caught in the respective widely-spaced elastic zones 82.

The crotch member 40 having been bonded to the front and rear waist members 20, 30 is provided on its garment-facing side with cover sheets 70 so as to cover the front and rear ends 41, 42 of the crotch member 40, respectively. Each of the cover sheets 70 may be formed of a fibrous nonwoven fabric or the like having a basis mass of about 10 to about 30 g/m². The cover sheet 70 is contoured by inner and outer ends 71, 72 extending in the transverse direction X and transversely opposite side edges 73 extending in the longitudinal direction Y. The side edges 73 are joined together with inner- and outer sheets 24, 25; 34, 35 of the front and rear waist members 20, 30 along the seam arrays 5. A length dimension of the cover sheet 70 in the longitudinal direction Y is set to be smaller than those of the front and rear waist members 20, 30, and a width dimension of the cover sheet 70 in the transverse direction X is set to be substantially equal to those of the front and rear waist members 20, 30.

The cover sheets 70 are attached to the crotch member 40 so as to overlap at least the respective widely-spaced elastic zones 82. The respective outer ends 71 are placed in the associated first narrowly-spaced elastic zones 81 and directly bonded to the outer sheets 25, 35 of the front and rear waist members 20, 30. The respective inner ends 72 are placed in the second narrowly-spaced elastic zones 83 and bonded at middle areas thereof to the crotch member 40 and at transversely opposite lateral areas extending outward beyond the crotch member 40 in the transverse direction X to the outer sheets 25, 35 of the front and rear waist members 20, 30. In this manner, the cover sheets 70 are bonded to the associated regions with hot melt adhesives (not shown) applied to substantially over the entire areas thereof.

The crotch member 40 is bonded to the respective garment-facing sides of the front and rear waist members 20, 30. In consequence, body waste, such as urine, would not move to the respective body-facing sides of the front and rear waist members 20, 30 even if body waste flows on the crotch member 40 in the longitudinal direction Y toward the front and rear waist members 20, 30. In this way, it is possible to protect the wearer against suffering from diaper rash due to direct contact of body waste with the wearer's skin. The crotch member 40 is bonded to the front and rear waist members 30, 40 in the first bonded regions 61, 62 and the second bonded regions 63, 64, respectively, and the pockets are defined in the respective front and rear waist regions 2, 3 by the first and second bonded regions 61, 62, 63, 64 and the non-bonded regions 65, 66. The pockets have openings directed toward the crotch region 4. More specifically, the vicinity of the transversely opposite side edge portions 43 of the crotch member 40 defining the respective non-bonded regions 65, 66, the vicinity of the respective inner ends 22, 32 of the front and rear waist members 20, 30 extending between the transversely opposite side edge portions 43 of the crotch member 40 and the vicinity of the front and rear ends 41, 42 of the crotch member 40 cooperate together to define the pockets. Each pocket defined in this manner is arranged to contain body waste moving along the crotch member 40 in the longitudinal direction Y and to prevent such body waste from flowing back toward the front and rear waist members 20, 30.

At least the second bonded region 63 in the front waist region 2 is shaped so that its outer edge as viewed in the transverse direction X extends (e.g., obliquely or in a step-wise manner) toward the imaginary longitudinal center line P-P and the crotch region 4. In consequence, an area over which the front waist member 20 is bonded to the crotch member 40 is correspondingly reduced and a region in which the crotch member is movable without being restricted by the front waist member 20 is correspondingly enlarged. This means that the crotch member 40 smoothly conforms to the movement of the wearer's thighs on the side of the front waist member 20. The region in which the crotch member 40 is movable without being restricted by the front waist member 20 is enlarged, and thereby facilitating the pocket defined by the non-bonded region 65 to be enlarged. Thus, the front waist region 2 can smoothly conform to the movement of the wearer' thighs and move over a range wider than that of the rear waist region 3. It should be appreciated that the second bonded region 64 in the rear waist region 3 also may be arranged in a manner similar to the second bonded region 63 in the front waist region 3.

The crotch member 40 attached to the respective garment-facing sides of the front and rear waist members 20, 30 is provided along the front and rear ends 41, 42 thereof with the cover sheets 70, 70 so as to cover these front and rear ends 41, 42. With such arrangement, it is possible to prevent the wearer's limb or garment from being caught by the front and rear ends 41, 42 of the crotch member 40 and causing the crotch member 40 to be peeled off from the front and rear waist members 20, 30. Certainly, there is a possibility that the wearer's foot might be caught by the crotch member 40 and, in consequence, the crotch member 40 might be pulled nearly away from the front and rear waist members 20, 30. However, the crotch member 40 is bonded to the front and rear waist members 20, 30 not only in the first and second bonded regions 61, 62, 63, 64 but also by the intermediary of the cover sheets 70, 70 and therefore the crotch region 40 would be unlikely to be completely peeled off from the front and rear waist members 20, 30. The first and second bonded regions 61, 62, 63, 64 are formed so as to define the non-bonded regions 65, 66 in the central region of the crotch member 40 and a joint strength of the crotch member 40 is necessarily lower than the case in which the non-bonded regions 65, 66 are not left. However, the cover sheets 70, 70 effectively prevent peeling off of the crotch member 40 from the front and rear waist members 20, 30.

Each of the cover sheets 70 is located so that a center line thereof bisecting its length dimension in the longitudinal direction Y is displaced outward from a center line of the associated front or rear waist member 20, 30 bisecting its length dimension in the longitudinal direction Y, i.e., each of the cover sheets 70 is displaced toward the associated one of the front and rear ends 21, 31. In other words, the cover sheets 70 are positioned outward in the longitudinal direction Y in the front and rear waist members 20, 30, respectively, and thereby assure the cover sheets 70 to be grasped together with the front and rear waist members 20, 30 when the helper or user grasps the upper end of the diaper 1 to put the diaper 1 on the wearer's body. The inner and outer sheets 24, 25, 34, 35 defining the front and rear waist members 20, 30 may be protected by the cover sheets 70 to protect these sheets from being damaged. Dimensions of the cover sheets 70 may be appropriately selected so far as these cover sheets 70 can effectively cover the crotch member's front and rear ends 41, 42 and a width dimension of the respective cover sheets 70 in the transverse direction X also may be appropriately selected so far as this dimension is larger than a distance by which the opposite fold lines 48 are spaced from each other in the transverse direction X. In this case, the side edges 73 of the respective cover sheets 70 are spaced in the transverse direction X inward from the associated side edges 23, 33 of the front and rear waist members 20, 30.

In the widely-spaced elastic zones 82, the elastic yarns or threads are sufficiently spaced one from another to assure that the helper or user's fingers may be smoothly caught between the adjacent elastic yarns or threads when the helper or user grasps upper portions of the diaper 1 to put the diaper 1 on the wearer's body or to take off the diaper 1 from the wearer's body and, for this purpose, adjustably pulls the diaper 1 up or down. In the course of putting the diaper 1 on the wearer's body in this manner, there is possibility that the front and rear waist members 20, 30 might be locally torn depending on the tear strength of these waist members 20, 30. However, the cover sheets 70 are located so as to overlap at least the widely-spaced elastic zones 82 and therefore the front and rear waist members 20, 30 would be unlikely to be torn due to such handling in the course of putting the diaper 1 on the wearer's body or taking off the diaper 1 from the wearer's body. The first and second narrowly-spaced elastics 81, 83 are at least partially free from coverage by the cover sheets 70. Specifically, the cover sheets' outer ends 71 are spaced inward from the front and rear waist members' outer ends 21, 31 in the longitudinal direction Y, and the cover sheets' inner ends 72 are spaced outward from the front and rear waist members' inner ends 22, 32 in the longitudinal direction Y. With such arrangement, the regions not including the cover sheets laminated thereon assure higher air-permeability in comparison with the regions including the cover sheets laminated thereon. In addition, a quantity of the cover sheets to be consumed can be reduced in comparison with the case in which the front and rear waist members 20, 30 are entirely covered with the cover sheets 70.

The cover sheets 70 are located so that the respective inner ends 72 are spaced outward from the associated inner ends 22, 32 of the front and rear waist members 20, 30 in the longitudinal direction Y. In consequence, the crotch member 40 overlapping the front and rear waist members 20, 30 are, in the vicinity of the inner ends 22, 32, not covered with the cover sheets 70, i.e., exposed. The section exposed in this manner can freely bulge toward the garment-facing side and thereby increase an area to be useful for containment of feces and urine. If the cover sheets 70 are dimensioned so that the respective inner ends 72 thereof lie just on the inner ends 22, 32 of the front and rear waist members 20, 30, a bulging range of the crotch member 40 toward the garment-facing side will be restricted and it will be impossible to increase the area to be useful for containment of body waste.

In the widely-spaced elastic zones 82, the number of the front and rear waist region elastics 26, 36 is smaller than that in the first and second narrowly-spaced elastic zones 81, 83 and the areas in which the front and rear waist members' inner sheets 24, 34 are directly bonded to the front and rear waist members' outer sheets 25, 35 are correspondingly enlarged and a joint strength between these inner and outer sheets 24, 25, 34, 35 is enhanced. With the joint strength enhanced in this manner, it is possible to put these inner and outer sheets in close contact with the wearer's body. It is also possible to reduce the likelihood that the diaper 1 may be torn in the course of putting the diaper 1 on the wearer's body or taking off the diaper 1 from the wearer's body by getting the helper's or user's fingers caught in at least the widely-spaced elastic zones 82.

In the second narrowly-spaced elastic zones 83 of the front and rear waist members 20, 30, the pitches of the front and rear waist elastics 26, 36 are enlarged in the vicinity of the front and rear waist regions' inner ends 22, 32 close to the crotch region 4. Consequently, a contractile force of the front and rear waist elastics 26, 36 is relatively low in these areas and, with the diaper 1 being put on the wearer's body, these areas are easily stretched and contracted. As a result, the pockets defined in the vicinity of the front and rear waist members' inner ends 22, 32 can be further enlarged in the transverse direction X. The front and rear waist elastics 26, 36 extending along the front and rear waist members' outer ends 21, 31 cooperate with the first crotch elastics 46 to surround almost an entire periphery of the leg-openings and thereby to put the leg-openings of the diaper 1 in close contact with the wearer's legs. It should be noted here that the leg-openings can be put in close contact with the wearer's legs and thereby leakage of body waste, such as urine, can be prevented without having the leg-openings excessively tightening the wearer's legs.

Transversely opposite laterals of the crotch member 40 are folded back along the fold lines 48 in the transverse direction X, the folded regions 49 are bonded to the front and rear waist members 20, 30 and the folded regions 49 are provided with the first and second crotch elastics 46, 47. With this arrangement, it is possible to put the folded regions 49 and particularly the transversely opposite side edge portions 43 of the crotch member 40 in close contact with the wearer's body. The liquid-absorbent structure 50 is placed between the fold lines 48 spaced from each other in the transverse direction X and thereby the liquid-absorbent structure 50 can be spaced from the wearer's body. In this way, diaper rash due to direct contact between body waste excreted on the liquid-absorbent structure 50 and the wearer's skin can be prevented and, at the same time, body waste can be prevented from leaking beyond the peripheral edges of the leg-openings.

While the first and second narrowly-spaced elastic zones 81, 83 and the widely-spaced elastic zones 82 are provided in the front and rear waist members 20, 30 almost symmetrically about the imaginary transverse center line Q-Q according to the present embodiment with respect to the placement as well as to the dimensioning, the present invention is not limited thereto. However, the widely-spaced elastic zones 82 are preferably formed in the front and rear waist members 20, 30 so as to be substantially symmetric about the imaginary transverse center line Q-Q. This is for the reason that the helper's or user's fingers will be caught by the diaper 1 at the same level when the helper or user grasps and pulls up any one of the front and rear waist members 20, 30 to put the diaper 1 on the wearer's body. In this way, the diaper 1 can be easily put on the wearer's body. While the first crotch elastic elements 46 are attached to the front and rear waist members 20, 30 evenly in the longitudinal direction Y according to the present embodiment, it is possible without departing from the scope of the present invention to bias these elastic elements 46 toward any one of the front and rear waist members 20, 30.

The number and the pitch of the front and rear waist elastics 26, 36 may be appropriately changed. With regard to the narrowly-spaced elastic zones and the widely-spaced elastic zones, it is desirable to form at least one narrowly-spaced elastic zone and at least one widely-spaced elastic zone in each of the front and rear waist members. This is for the reason that the widely-spaced elastic zone facilitates the helper's or user's finger to be caught between each pair of the adjacent waist elastics and the narrowly-spaced elastic zone assures the diaper 1 to be kept in close contact with the wearer's body. The widely-spaced elastic zones are preferably formed so as to be spaced inward from the front and rear waist members' outer ends 21, 31 by about 40 to about 80 mm in consideration that the spacing in such a range allows the helper's or user's fingers to be smoothly caught by the widely-spaced elastic zones in the course of pulling the diaper 1 upward along the wearer's body. Each pair of the adjacent front and rear waist elastics 26, 36 in widely-spaced elastic zones is preferably spaced from each other by about 15 to about 50 mm.

Figure 7:
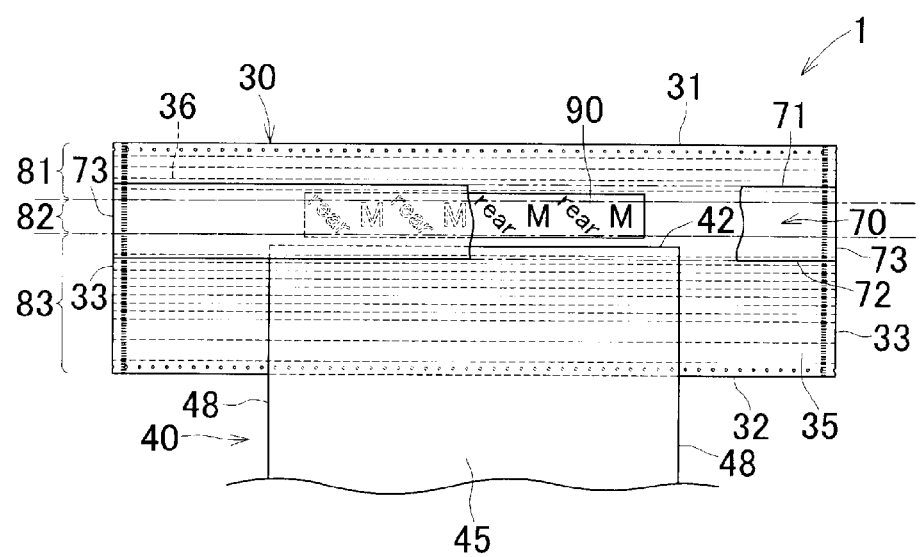
FIG. 7 A partially cutaway plan view of the diaper according to another embodiment of the present invention.

FIG. 7 is a partially cutaway developed plan view illustrating the rear waist region 3 of the diaper 1 according to another embodiment as viewed from the garment-facing side. As illustrated, a display sheet 90 adapted to display graphics and/or letters (including trademarks and trade names) and/or numbers is sandwiched between the rear waist member's outer sheet 35 and the cover sheet 70. The other features are identical to those illustrated in FIGS. 1 through 6 and details thereof will be not repetitively described hereunder. The display sheet 90 may be formed of a liquid-impervious but moisture-pervious plastic film and bear thereon appropriate display elements, such as graphics and/or letters and/or numbers to indicate to the helper or user that the side having this display sheet 90 is the rear waist region 3 when the diaper 1 is put on the wearer's body. According to the present embodiment, letters "rear side" and a letter "M" indicating the diaper's size are displayed.

The cover sheet 70 has a total luminous transmittance allowing the graphics and/or the letters and/or numbers of the display sheet 90 to be visually recognized through the cover sheet 70 laminated thereon. In this way, the display elements, such as the graphics and/or the letters and/or numbers can be visually recognized from the garment-facing side of the diaper 1 and thereby the front side and the rear side of the diaper 1 can be discriminated.

The display sheet 90 is attached to the diaper 1 so as to overlap the widely-spaced elastic zone 82 in the rear waist member 30. A contraction percentage in the transverse direction X of the widely-spaced elastic zone 82 is smaller than those of the first and second narrowly-spaced elastic zones 81, 83 and wrinkles developed in the widely-spaced elastic zone 82 due to contraction are correspondingly less remarkable. In addition, the display sheet 90 and the cover sheet 70 are laminated on the widely-spaced elastic zone 82 to enhance stiffness thereof and, in consequence, development of wrinkles is further reliably restricted. With less wrinkles developed, it becomes easier to visually recognize the graphics and/or the letters and/or numbers on the display sheet 90. There is a possibility that the helper's or user's finger might be caught by the widely-spaced elastic zone 82 in the course of putting the diaper 1 on the wearer's body. However, the display sheet 90 laminated with this widely-spaced elastic zone 82 serves to improve the tear strength of this zone 82 and thereby to reduce the likelihood of the rear waist member 30 being torn, at least in the zone laminated with the display sheet 90.

According to the present embodiment, length and width dimensions of the display sheet 90 in the longitudinal direction Y as well as in the transverse direction X are smaller than those of the cover sheet 70 and, particularly, the width dimension of the display sheet 90 in the transverse direction X is set to be smaller than a distance between the fold lines 48 of the crotch member 40. Alternatively, the display sheet 90 may be implemented to have a size sufficiently large to cover the sections of the crotch member 40 overlapping the front and rear waist members 20, 30, respectively. In this case, the display sheets 90 can serve also to prevent leakage of body waste occurring in joints between the crotch member 40 and the front and rear waist members 20, 30. It is also possible to display the display elements, such as the graphics and/or the letters and/or numbers, directly on the cover sheet 70 or the crotch member 40 without use of the display sheet 90.

While the display sheet 90 is sandwiched between the cover sheet 70 and the rear waist member's outer sheet 35 according to the present embodiment, it is also possible without departing from the scope of the present invention to sandwich the display sheet 90 between the inner and outer sheets 34, 35 of the rear waist member 30 or to attach the display sheet 90 to the front waist member 20 or to attach the display sheet 90 to both the front and rear waist members 20, 30.

The component members of the diaper 1 are not limited to those described in this specification but the other various types of material widely used in the relevant technical field may be used without limitation. The terms "first" and "second" used in the specification and claims of the present application are used merely to distinguish similar elements, similar positions or similar means.

One or more aspects described above may be arranged in at least the following:

There is provided a disposable wearing article having longitudinal and transverse directions and including a body-facing side for facing a wearer's body, a garment-facing side for facing away from the wearer's body, front and rear waist regions and a crotch region extending between the front and rear waist regions in the longitudinal direction, front and rear waist members defining the front and rear waist regions, respectively, and a crotch member defining the crotch region and joined to the front and rear waist members.

The crotch member has front and rear ends extending in the transverse direction, at least the front and rear ends are joined to the garment-facing side of the front and rear waist members, respectively, the crotch member is provided on the garment-facing side with cover sheets that cover the front and rear ends of the crotch member; and a length dimension of the cover sheets in the longitudinal direction is smaller than those of the front and rear waist members.

The aspects described in the above paragraph [0041] may include the following embodiments and any technically possible combination thereof:

(i) A width dimension of the cover sheets in the transverse direction is equal to those of the front and rear waist members.

(ii) The front and rear waist members are respectively contoured by outer ends extending in the transverse direction and inner ends between the outer ends as viewed in the longitudinal direction; the cover sheets are respectively contoured by outer ends extending in the transverse direction and inner ends between the outer ends as viewed in the longitudinal direction; and the cover sheets' inner ends are respectively spaced outward from associated the front and rear waist members' inner ends.

(iii) Between the crotch member and the front and rear waist members, bonded regions in which these members are bonded to each other and non-bonded regions in which these members are not bonded to each other are defined; the bonded regions include first bonded regions extending along the crotch member's front and rear ends in the transverse direction, and second bonded regions extending in the longitudinal direction on both transversely opposite sides of the first bonded regions; and each the non-bonded region is surrounded by the respective first and second bonded regions to form pockets are defined in the respective front and rear waist regions by the first and second bonded regions and the non-bonded regions wherein pockets have openings directed toward the crotch region.

(iv) The front and rear waist members are respectively provided with a plurality of front and rear waist elastics spaced one from another in the longitudinal direction and attached under tension and in a contractible manner to the front and rear waist members so that widely-spaced elastic zones in which each pair of the adjacent elastics are widely spaced from each other are defined.

(v) The cover sheets at least partially overlap the widely-spaced elastic zones.

(vi) Narrowly-spaced elastic zones in which each pair of the adjacent elastics are spaced from each other more narrowly than in the widely spaced elastic zones are defined on both sides of respective the widely-spaced elastic zones as viewed in the longitudinal direction of the front and rear waist members, and the first bonded regions are formed in regions corresponding to the narrowly-spaced elastic zones lying on inner sides as viewed in the longitudinal direction.

(vii) The crotch member is provided along transversely opposite side edges thereof with crotch elastics, and the second bonded regions are formed along regions in which the crotch elastics are attached to the crotch member.

(viii) Transversely opposite side edges of the crotch member are folded back inward in the transverse direction along fold lines extending in the longitudinal direction, and regions folded in this manner respectively face the front and rear waist members and define the second bonded regions.

(ix) A liquid-absorbent structure contoured by front and rear ends and transversely opposite side edges is placed on the body-facing side of the crotch member so that the front and rear ends of the liquid-absorbent structure lie between the crotch member's front and rear ends, and the transversely opposite side edges of the liquid-absorbent structure lie between the fold lines as viewed in the transverse direction.

(x) The front and rear waist members are joined to each other along the front and rear waist members' transversely opposite side edges extending in the longitudinal direction to be maintained in an annular shape.

(xi) The widely-spaced elastic zone in at least one of the front and rear waist members is provided with a display sheet including display elements.

(xii) A width dimension of the second bonded regions is reduced gradually or in stepwise manner toward the crotch region and toward a longitudinal center line P-P that bisects a width dimension of the article in the transverse direction.

(xiii) An outer edge of each of the second bonded regions extends obliquely or in stepwise manner toward the crotch region and toward a longitudinal center line P-P that bisects a width dimension of the article in the transverse direction.

(xiv) The cover sheets' outer ends are respectively spaced inward from associated the front and rear waist members' outer ends.

(xv) Each of the front and rear waist members is respectively provided with a plurality of respective front or rear waist elastics spaced one from another in the longitudinal direction and attached under tension and in a contractible manner to the respective front or rear waist member so as to define a widely-spaced elastic zone, a first narrowly-spaced elastic zone in which each pair of the adjacent elastics are spaced from each other more narrowly than in the widely-spaced elastic zone, and which is positioned outward of the widely-spaced elastic zone as viewed in the longitudinal direction, and a second narrowly-spaced elastic zone in which each pair of the adjacent elastics are spaced from each other more narrowly than in the widely-spaced elastic zone, and which is positioned inward of the widely-spaced elastic zone as viewed in the longitudinal direction, and wherein the respective cover sheet has the outer end placed in the first narrowly-spaced elastic zone, and the inner end placed in the second narrowly-spaced elastic zone.

(xvi) The second narrowly-spaced elastic zone in at least one of the front and rear waist members have a pitch between the respective front or rear waist elastics, the pitch being enlarged in the vicinity of the inner end of the respective front or rear waist region adjacent the crotch region.

(xvii) Each of the cover sheets has a center line bisecting a length dimension thereof in the longitudinal direction, the respective front or rear waist member has a center line bisecting a length dimension thereof in the longitudinal direction, and the center line of the cover sheet is displaced outward from that of the respective front or rear waist member.

This application claims the benefit of Japanese Application No. 2010-195012 the entire disclosure of which is incorporated by reference herein.

REFERENCE SIGNS LIST

1 diaper (disposable wearing article)
2 front waist region
3 rear waist region
4 crotch region
20 front waist member
21 outer end of front waist member
22 inner end of front waist member
23 side edges of front waist member
30 rear waist member
31 outer end of the rear waist member
32 inner end of the rear waist member
33 side edges of rear waist member
26 front waist elastics
36 rear waist elastics 40 crotch region
41 front end of crotch member
42 rear end of crotch member
43 side edge portions of crotch member
46 first crotch elastics
47 second crotch elastics
48 fold lines
50 liquid-absorbent structure
51 front end of liquid-absorbent structure
52 rear end of liquid-absorbent structure
53 side edges of liquid-absorbent structure
61, 62 first bonded regions
63, 64 second bonded regions
65, 66 non-bonded regions
70 cover sheet
71 outer end of cover sheet
72 inner end of cover sheet
81 first narrowly-spaced elastic zones
82 widely-spaced elastic zones
83 second narrowly-spaced elastic zones
90 display sheet
x transverse direction
Y longitudinal direction

The invention claimed is:

1. A disposable wearing article having longitudinal and transverse directions, comprising:
    a body-facing side for facing a wearer's body,
    a garment-facing side for facing away from the wearer's body,
    front and rear waist regions and a crotch region extending between the front and rear waist regions in the longitudinal direction,
    front and rear waist members defining the front and rear waist regions, respectively, and
    a crotch member defining the crotch region and joined to the front and rear waist members,
    wherein
    the crotch member has front and rear ends extending in the transverse direction,
    at least the front and rear ends are joined to the garment-facing side of the front and rear waist members, respectively,
    the crotch member is provided on the garment-facing side with cover sheets that cover the front and rear ends of the crotch member; and
    a length dimension of the cover sheets in the longitudinal direction is smaller than those of the front and rear waist members.

2. The disposable wearing article defined by claim 1, wherein a width dimension of the cover sheets in the transverse direction is equal to those of the front and rear waist members.

3. The disposable wearing article defined by claim 1, wherein
    the front and rear waist members are respectively contoured by outer ends extending in the transverse direction and inner ends between the outer ends as viewed in the longitudinal direction;
    the cover sheets are respectively contoured by outer ends extending in the transverse direction and inner ends between the outer ends as viewed in the longitudinal direction; and
    the cover sheets' inner ends are respectively spaced outward from associated the front and rear waist members' inner ends.

4. The disposable wearing article defined by claim 1, wherein
    between the crotch member and the front and rear waist members, bonded regions in which these members are bonded to each other and non-bonded regions in which these members are not bonded to each other are defined;
    the bonded regions comprise first bonded regions extending along the crotch member's front and rear ends in the transverse direction, and second bonded regions extending in the longitudinal direction on both transversely opposite sides of the first bonded regions; and
    each the non-bonded region is surrounded by the respective first and second bonded regions to form pockets are defined in the respective front and rear waist regions by the first and second bonded regions and the non-bonded regions wherein pockets have openings directed toward the crotch region.

5. The disposable wearing article defined by claim 1, wherein the front and rear waist members are respectively provided with a plurality of front and rear waist elastics spaced one from another in the longitudinal direction and attached under tension and in a contractible manner to the front and rear waist members so that widely-spaced elastic zones in which each pair of the adjacent elastics are widely spaced from each other are defined.

6. The disposable wearing article defined by claim 5, wherein the cover sheets at least partially overlap the widely-spaced elastic zones.

7. The disposable wearing article defined by claim 5, wherein
    narrowly-spaced elastic zones in which each pair of the adjacent elastics are spaced from each other more narrowly than in the widely spaced elastic zones are defined on both sides of respective the widely-spaced elastic zones as viewed in the longitudinal direction of the front and rear waist members, and
    the first bonded regions are formed in regions corresponding to the narrowly-spaced elastic zones lying on inner sides as viewed in the longitudinal direction.

8. The disposable wearing article defined by claim 4, wherein the crotch member is provided along transversely opposite side edges thereof with crotch elastics, and the second bonded regions are formed along regions in which the crotch elastics are attached to the crotch member.

9. The disposable wearing article defined by claim 4, wherein transversely opposite side edges of the crotch member are folded back inward in the transverse direction along fold lines extending in the longitudinal direction, and regions folded in this manner respectively face the front and rear waist members and define the second bonded regions.

10. The disposable wearing article defined by claim 9, wherein a liquid-absorbent structure contoured by front and rear ends and transversely opposite side edges is placed on the body-facing side of the crotch member so that the front and rear ends of the liquid-absorbent structure lie between the crotch member's front and rear ends, and the transversely opposite side edges of the liquid-absorbent structure lie between the fold lines as viewed in the transverse direction.

11. The disposable wearing article defined by claim 1, wherein the front and rear waist members are joined to each other along the front and rear waist members' transversely opposite side edges extending in the longitudinal direction to be maintained in an annular shape.

12. The disposable wearing article defined by claim 5, wherein the widely-spaced elastic zone in at least one of the front and rear waist members is provided with a display sheet including display elements.

13. The disposable wearing article defined by claim 4, wherein a width dimension of the second bonded regions is reduced gradually or in stepwise manner toward the crotch region and toward a longitudinal center line that bisects a width dimension of the article in the transverse direction.

14. The disposable wearing article defined by claim 4, wherein an outer edge of each of the second bonded regions extends obliquely or in stepwise manner toward the crotch region and toward a longitudinal center line that bisects a width dimension of the article in the transverse direction.

15. The disposable wearing article defined by claim 3, wherein
   the cover sheets' outer ends are respectively spaced inward from associated the front and rear waist members' outer ends.

16. The disposable wearing article defined by claim 3, wherein each of the front and rear waist members is respectively provided with a plurality of respective front or rear waist elastics spaced one from another in the longitudinal direction and attached under tension and in a contractible manner to the respective front or rear waist member so as to define
   a widely-spaced elastic zone,
   a first narrowly-spaced elastic zone in which each pair of the adjacent elastics are spaced from each other more narrowly than in the widely-spaced elastic zone, and which is positioned outward of the widely-spaced elastic zone as viewed in the longitudinal direction, and
   a second narrowly-spaced elastic zone in which each pair of the adjacent elastics are spaced from each other more narrowly than in the widely-spaced elastic zone, and which is positioned inward of the widely-spaced elastic zone as viewed in the longitudinal direction, and
   wherein the respective cover sheet has the outer end placed in the first narrowly-spaced elastic zone, and the inner end placed in the second narrowly-spaced elastic zone.

17. The disposable wearing article defined by claim 3, wherein
   the second narrowly-spaced elastic zone in at least one of the front and rear waist members have a pitch between the respective front or rear waist elastics, the pitch being enlarged in the vicinity of the inner end of the respective front or rear waist region adjacent the crotch region.

18. The disposable wearing article defined by claim 3, wherein
   each of the cover sheets has a center line bisecting a length dimension thereof in the longitudinal direction,
   the respective front or rear waist member has a center line bisecting a length dimension thereof in the longitudinal direction, and
   the center line of the cover sheet is displaced outward from that of the respective front or rear waist member.

\* \* \* \* \*